(12) United States Patent  
Eckstein et al.

(10) Patent No.: US 8,540,688 B2  
(45) Date of Patent: Sep. 24, 2013

(54) VACUUM GENERATION DEVICE FOR VACUUM TREATMENT OF WOUNDS

(75) Inventors: Axel Eckstein, Heidenheim (DE); Juergen Hofstetter, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 13/469,106

(22) Filed: May 11, 2012

(65) Prior Publication Data

US 2012/0289914 A1   Nov. 15, 2012

Related U.S. Application Data

(60) Provisional application No. 61/457,845, filed on Jun. 17, 2011.

(30) Foreign Application Priority Data

May 13, 2011 (DE) .......................... 10 2011 075 844

(51) Int. Cl.  
*A61M 1/00* (2006.01)

(52) U.S. Cl.  
USPC ........... 604/305; 604/306; 604/307; 604/308; 604/315; 604/316; 604/317; 604/318; 604/319; 604/320; 604/321; 604/322; 604/323; 604/540; 604/541; 604/542; 604/543; 604/544; 604/902; 606/131

(58) Field of Classification Search  
USPC .......................................... 604/313, 315, 316  
See application file for complete search history.

(56) References Cited

U.S. PATENT DOCUMENTS

| | | | |
|---|---|---|---|
| 8,034,037 B2 * | 10/2011 | Adams et al. | ................. 604/313 |
| 2004/0073151 A1 | 4/2004 | Weston | |
| 2008/0082059 A1 | 4/2008 | Fink | |
| 2009/0012441 A1 | 1/2009 | Mulligan | |
| 2010/0042074 A1 | 2/2010 | Weston | |
| 2010/0298792 A1 * | 11/2010 | Weston et al. | ................. 604/319 |
| 2010/0318071 A1 | 12/2010 | Wudyka | |
| 2011/0008179 A1 | 1/2011 | Turner | |
| 2011/0040268 A1 | 2/2011 | Eckstein | |
| 2011/0040288 A1 | 2/2011 | Eckstein | |
| 2011/0106058 A1 | 5/2011 | Svedman | |
| 2011/0245757 A1 * | 10/2011 | Myntti et al. | .................. 604/22 |

FOREIGN PATENT DOCUMENTS

| | | |
|---|---|---|
| EP | 0 777 504 | 6/1997 |
| EP | 0 988 865 | 3/2000 |
| EP | 1 905 465 | 4/2008 |
| WO | WO 03/005943 | 1/2003 |
| WO | WO 2007/030599 | 3/2007 |
| WO | WO 2009/047524 | 4/2009 |

* cited by examiner

*Primary Examiner* — Tatyana Zalukaeva  
*Assistant Examiner* — Ilya Treyger  
(74) *Attorney, Agent, or Firm* — Paul Vincent

(57) ABSTRACT

A portable device (2) to generate a vacuum for the medical treatment of wounds on the bodies of humans or animals has a vacuum-producing suction pump (90) in a first housing part (4) of the device and a vessel (10) for receiving body liquids. Vacuum is applied for vacuum communication between the suction pump (90), the vessel (10) and a suction tube (82) leading to the body. A pressure sensor (94) measures the pressure in a tube section (88) and a programmable electronic control unit (100) controls the suction pump (90) in dependence on pressure values measured by the pressure sensor (94). The electronic control unit (100) deactivates the suction pump (90) if a rate of change in pressure ($\Delta p/\Delta t$) detected by the pressure sensor (94) exceeds a defined threshold value toward decreasing vacuum.

12 Claims, 10 Drawing Sheets

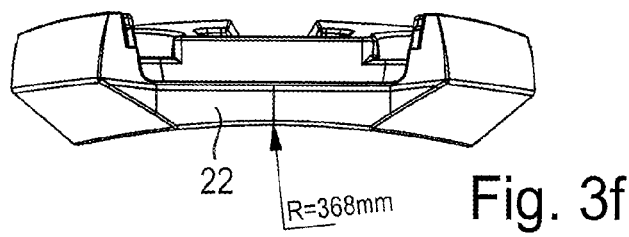
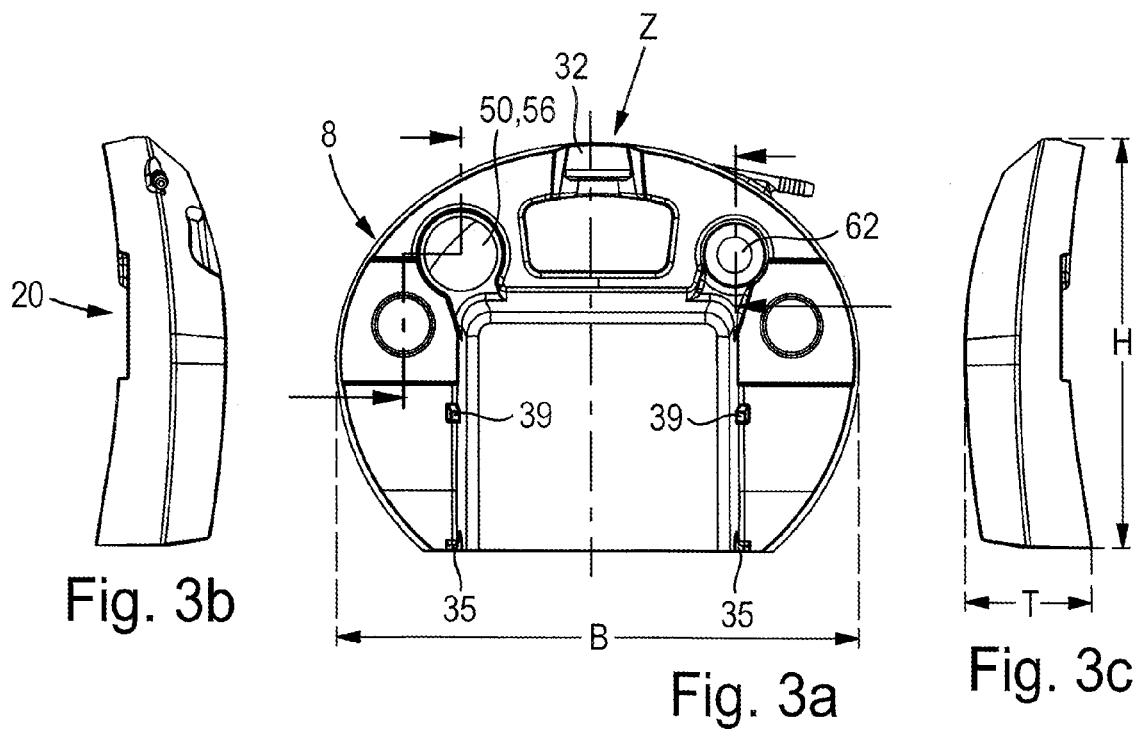
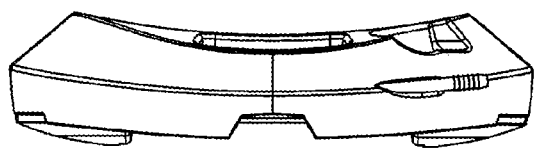

VACUUM GENERATION DEVICE FOR
VACUUM TREATMENT OF WOUNDS

This application claims Paris Convention priority of DE 10 2011 075 844.5 filed May 13, 2011 and benefit of Provisional application 61/457,845 filed Jun. 17, 2011, the entire disclosures of which are hereby incorporated by reference.

BACKGROUND OF THE INVENTION

The invention relates to a portable device suitable for carrying on the body of a user to generate a vacuum for the medical vacuum treatment of wounds on the bodies of humans or animals, comprising a vacuum-producing suction pump in a first housing part of the device, a vessel for receiving body liquids, in particular, wound exudates suctioned out of a wound, wherein the vessel can be releasably attached to the first housing part of the device and a vacuum can be applied by the suction pump in the attached condition, and wherein a connection is provided on the vessel for a suction tube leading to the body, so that vacuum communication between the suction pump, the vessel and the suction tube leading to the body can be established, a pressure sensor that is disposed between the vessel and the suction pump in order to measure the pressure in one tube section, a programmable electronic control unit that can control the suction pump at least taking account of defined and/or definable parameters and the pressure values measured by the pressure sensor. Where it is stated above that a device is portable this means that the patient can carry the device so that he is mobile and his wound can nevertheless be constantly treated, i.e. without interruption. The portable device can be held and carried on the patient's body by means of any attachment means, in particular and preferably in the form of a flexible belt or a shoulder carrying strap. A portable device of the type stated here can, of course, also be used in stationary operation, that is, detached from the body of the patient; in this case, it can, for example, be affixed to a care bed or next to a care bed.

Devices for vacuum treatment have already been described several times, in particular by US 2004/0073151 A1, WO 2009/047524 A2, WO 2007/030599 A2, or EP 1 905 465 A1, EP 777 504 B, and by DE 10 2009 038 130 A, and DE 10 2009 038 131 A of the assignee.

In such devices for the vacuum treatment of wounds, a suction pump communicates with the wound or the region of the wound through a suction tube, wherein a wound dressing with a cover material that is impermeable to air is provided for air-tight closure of the wound and the region of the wound, so that a vacuum can be established in the wound space and liquids from the wound space can be suctioned into the aforementioned vessel.

The term vacuum in connection with this invention refers to a lower air pressure than ambient air pressure (atmospheric pressure), in particular inside the wound dressing. The cover material of a wound dressing for air-tight closure of a wound space must therefore be constituted such that it can withstand the established pressure difference so that the vacuum in the wound space can be produced in the first instance and then maintained. However, the wound dressing and covering material typically exhibit a certain degree of compliance. In vacuum therapy for wound treatment, the vacuum is quantitatively expressed as the pressure difference between the ambient air pressure and the air pressure applied underneath the cover material. In vacuum therapy, this pressure difference is typically no more than 250 mmHg (mm of mercury) (1 mmHg=1 Torr=133.322 Pa). This vacuum range not exceeding 250 mmHg has proven advantageous for wound healing. A preferred vacuum range is between 10 and 150 mmHg.

The vacuum applied to the wound using the device can, in typical vacuum therapy, either be kept essentially constant over time or it can vary over time, in particular, cyclically, which can be implemented using an appropriately constituted and programmed control device on the facility producing the vacuum, in particular, depending on further parameters.

To apply the vacuum and preferably also to suction away body fluids, a preferably flexible suction tube, for example, in the form of a drainage tube, is provided that communicates at one end through a port in the region of the wound cover material with the wound environment or the wound space and at the other end with the vessel mentioned above for receiving body fluids or with the facility producing the vacuum.

In addition to the vacuum therapy of wounds, other applications of the device described here are conceivable for providing a vacuum for medical applications, in particular, the removal by suction of any body fluids in medical incontinent care, the care of stoma patients, or for the removal by suction of wound exudates, possibly, using rinsing liquids, and also without the application of a vacuum over considerable periods.

Based on this kind of portable device for generating a vacuum for medical applications, the object of this invention is to further optimize user-friendliness and reliability so that a less technically skilled user or patient is given the feeling of reliably mastering the method of operation of the device.

SUMMARY OF THE INVENTION

This object is inventively achieved in a device of this kind in that the electronic control unit is constituted such that the suction pump is deactivated if, during continuing closed-loop vacuum control operation, a rate of change in pressure ($\Delta p/\Delta t$) detected by means of the signals from the pressure sensor exceeds a defined threshold value toward decreasing vacuum, that is, toward an increase in absolute pressure.

Deactivation of the suction pump in this sense means an interruption in operation of the device until a restart that can be triggered easily, that is, the currently running closed-loop pressure control operation and therefore control of the pump are permanently interrupted until the user initiates a restart and therefore a new operating cycle. With the present invention, it was ascertained that, especially on devices for the vacuum treatment of wounds that can be carried on the body of the patient, the most frequent cause of maloperation is that the vessel for receiving body liquids becomes detached from the first housing part of the device in which the suction pump and the electronic control components are located, resulting in undifferentiated control states. For example, while a vacuum open-loop or closed-loop control is active, if the vessel becomes detached from the first housing part of the portable device, in terms of closed-loop-control, this can cause the electronic control unit to control the suction pump toward increasing suction power, which is frequently associated with the development of noise and can worry the user and also make control actions by the user necessary. This situation can also occur if a vessel fully or largely filled with liquid is deliberately replaced with a new vessel.

With the inventive design of the device, on the other hand, it is ensured that, during continuing closed-loop vacuum control operation, the vacuum-producing suction pump is permanently deactivated by the electronic control unit as soon as an abrupt rate of pressure change ($\Delta p/\Delta t$) toward decreasing vacuum, that is, an abrupt increase in absolute pressure, is detected. This abrupt pressure increase is detected via a rate of pressure change and identified as such by the electronic control unit by means of the signals of the pressure sensor. This is done by ascertaining whether the rate of pressure change exceeds a defined threshold value. If this is the case, the pump is permanently deactivated until a subsequent restart, as explained. In this way, no undefined states arise that could confuse the user as to which control measures to take. Instead, the user can become used to having to restart the device in the usual way, by the action that is familiar to him, after replacing the vessel.

A similar situation can arise, in particular, if, during mobile operation of the device, a suction tube becomes detached from its fastening gland at the vessel end or wound dressing end or also if a very large leak occurs due to damage to a tubing means. This invention is especially important for mobile use of portable devices of the type stated here, because patients equipped with such a portable device are reliant on themselves when far away from a clinical institution and therefore complex devices should exhibit a minimum variety of states that the patient must understand and respond to with an operator action. If the same state, that is, operation deactivated, is communicated to the technically unskilled user or patient, to which he must always respond in the same way, that is, by starting up again, it will be much easier for him. With the inventive design, operability of the device is therefore easier overall and therefore also less prone to maloperations, thus increasing overall reliability.

The aforementioned threshold value for the rate of pressure change ($\Delta p/\Delta t$) toward decreasing vacuum, that is, toward an increase in absolute pressure is preferably at least 40 mmHg/s (mm of mercury column per second). It can, in particular, be implemented with 45, 50, or 55 mmHg/s in the programmable electronic control unit.

It further proves advantageous if an output or display unit for generating a signal is provided that visually or acoustically communicates an abrupt increase in pressure with a rate of pressure change above the threshold value and therefore deactivation of the suction pump. In this way, it is possible to communicate to the user or patient that he must restart the device, in particular, after reattachment of the vessel or after replacement with a new vessel.

In a further development of the invention, it can also prove advantageous if an output or display unit is provided that is constituted for wireless communication of a signal to an external receiver that communicates the abrupt pressure increase with a rate of pressure change above the threshold value and the resulting deactivation of the suction pump to an external receiver. The external receiver may be, for example, a ward center in a hospital or a care control center or similar so that the deactivation of the closed-loop pressure control operation or the suction pump is communicated thereto and further steps can be introduced from there, in particular, in the case of patients requiring care.

The inventive device can further comprise an aeration valve, which can be controlled by the control unit and which can be connected to the wound space via an aeration tube provided in addition to the suction tube so that the wound space can be aerated with fresh air. The threshold value stored in the control unit for the rate of pressure change ($\Delta p/\Delta t$) is chosen sufficiently high and the flow through the aeration valve is selected such that a pressure increase during normal operation of the aeration valve remains below this threshold value.

The invention proves particularly advantageous on a device that is further characterized by a facility, which can be controlled by the electronic control unit to supply a rinsing liquid or other fluid that can be connected to the wound space via a rinsing tube provided in addition to the suction tube, so that rinsing liquid or another fluid, in particular, with components having a therapeutic effect, can be supplied to the wound space. In such a case, it proves especially advantageous if the electronic control unit is further constituted such that on deactivation of the suction pump, the facility for supplying the rinsing liquid or another fluid is also deactivated. It proves much more reliable to deactivate this facility for supplying a rinsing liquid during vessel change or another operating disturbance together with the suction pump permanently until a restart of the device.

There are devices for vacuum treatment of wounds of the inventive kind for example, EP 777 504 A, in which the aim is to determine via a filling level sensor whether the vessel is full and must be replaced with a new vessel; if the vessel is recognized as full, the suction pump is deactivated, that is, the closed-loop pressure control operation is interrupted. With this invention, however, this has been recognized as disadvantageous because, especially in the case of portable devices in mobile operation, filling level monitoring of the vessel of the aforementioned type frequently issues incorrect information. For example, due to movements of the user, for instance, when bending down, a vessel-full state is detected that actually does not apply. Moreover, deactivation of the suction pump usually results much too early in reduction of the vacuum. Frequently, an unused vessel is not available or such care measures have to be deferred. In a further embodiment of this invention, it is therefore proposed that the electronic control unit is constituted such that it does not deactivate the suction pump on correct or incorrect detection of a vessel-full state, but the defined closed-loop vacuum control operation is continued. In this way, it is thus ensured that the closed-loop vacuum control operation is not interrupted too early or accidentally. Even if it is detected with certainty that vessel replacement is appropriate, it proves advantageous if normal closed-loop vacuum control operation is continued via the electronic control unit, i.e. the suction pump maintains the vacuum on the vessel in the manner predetermined in the control. If the vessel then becomes detached from the first housing part, i.e. the base of the device becomes detached, an abrupt pressure increase is determined based on determination of the rate of pressure change and the suction pump is only permanently deactivated then.

Irrespective of this, it proves advantageous if the electronic control unit is constituted such that it does not deactivate, that is, permanently shut down the suction pump, so that it has to be restarted on a vacuum increase, that is, on a decrease in the absolute pressure in the tube section between vessel and suction pump that points to increasing filling of the vessel or other, in particular, temporary undefined states or faults, in particular, due to the movement of the user, but instead the defined closed-loop vacuum control operation is continued. According to this inventive idea, therefore, closed-loop vacuum control operation is only deactivated on a decreasing vacuum (increase in absolute pressure) and not on an increasing vacuum (decrease in absolute pressure). Building on the preceding inventive idea, an increasing vacuum (decrease in absolute pressure), in particular, an abruptly increasing vacuum points to a vessel-full state, that is, in particular, when a filter is used that is permeable to air but not permeable to liquid in the region of a vessel outlet to the tube section leading to the suction pump. If the liquid level in the vessel rises up to or over this filter, the filter will block increasingly and result in an increase in vacuum in the tube section between the vessel and suction pump, which is, in turn, detected by the pressure sensor.

The object of the invention is also a method with the characteristics of the method claims.

Further characteristics, details, and advantages of the invention result from the appended patent claims and from the drawings and the following description of a preferred embodiment of the invention. The drawings show:

BRIEF DESCRIPTION OF THE DRAWING

FIGS. 3a to i various views of a second housing part of the device according to FIG. 1, constituting a vessel to receive body fluids;

DESCRIPTION OF THE PREFERRED EMBODIMENT

First, based on FIGS. 1 to 5, two embodiments of a portable device 2 for providing a vacuum for medical applications are described that differ only in respect of their dimensioning and the constitution of a vessel, still to be described, for receiving body liquids. Thereafter, based on FIG. 6, the inventive constitution of the control components of the portable device 2 is described.

Figure 6:
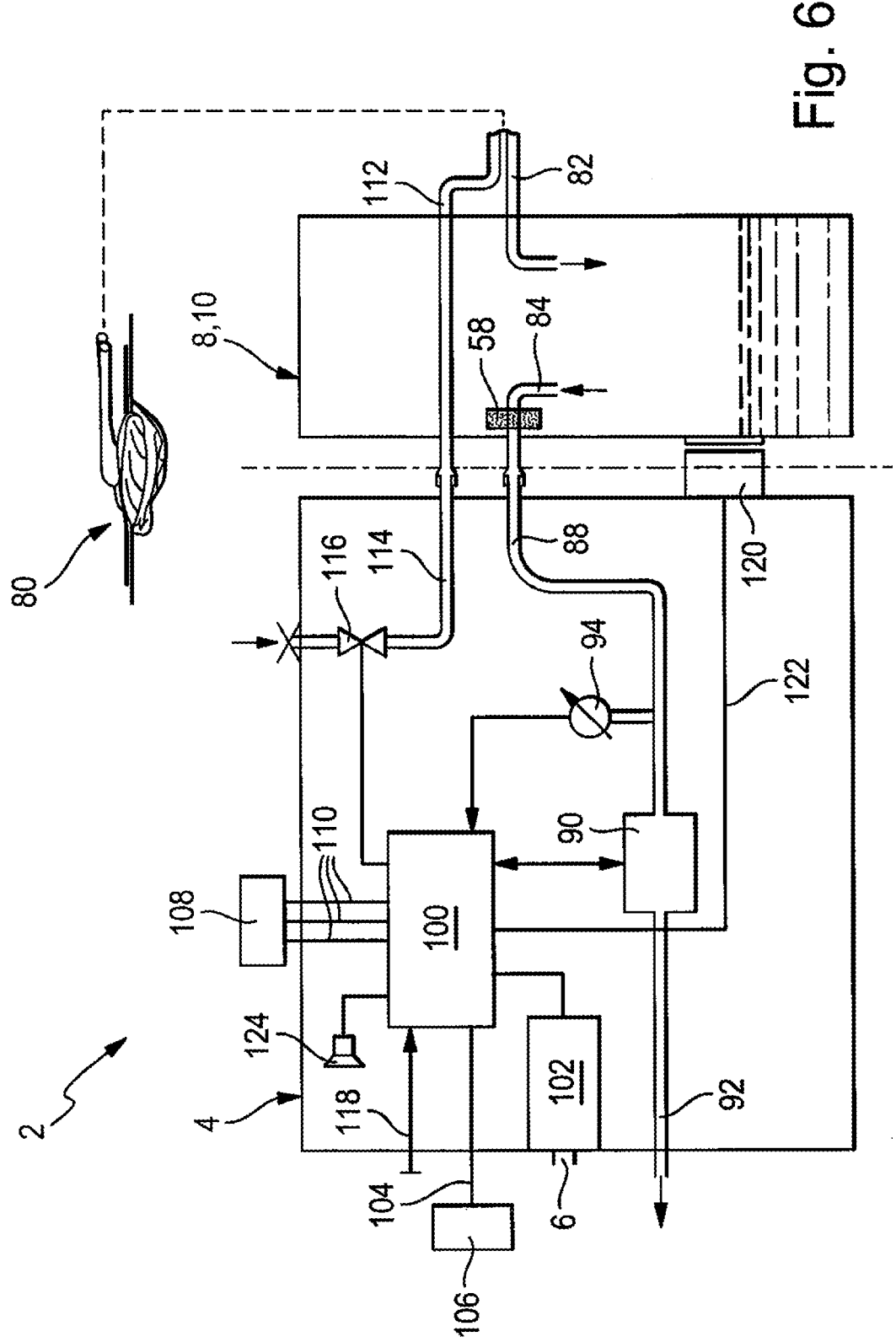
FIG. 6 a schematic view of the first and second housing part with an indication of the control components.

FIGS. 1a to e show a first embodiment of a portable device 2 for the provision of the vacuum for medical applications. The device comprises a first housing part 4 in which a vacuum-producing device in the form of an air suction pump 90 shown in FIG. 6 and electrical and electronic control components for the device are accommodated completely, including batteries or preferably rechargeable batteries. A recharging connection for the batteries is designated by reference symbol 6. Moreover, the device 2 comprises a second housing part 8 that is also a vessel 10 for receiving body fluids, in particular, for receiving wound exudates suctioned away from a wound. The entire second housing part 8 is preferably constituted as a disposable single-use item. In its upper region, a connection gland 12 for a suction tube 82 first shown in FIG. 6 is provided that can, for example, lead to a wound dressing 80 that closes the wound pressure-tight when the device 2 is used in the vacuum therapy of wounds and there it can, for example, communicate with the wound space through a port to apply and maintain a vacuum to the wound space and to suction away wound exudates into the vessel 10. For this purpose, the vessel 10 communicates with the suction pump. Further, a connection 13 is shown for an optional measuring or rinsing duct that is guided to the wound, like the suction tube. This connection passes through the second housing part 8 and exits into the first housing part 4, from where, for example, air as the rinsing medium can be applied to the measuring or rinsing duct and/or pressure in this measuring or rinsing duct can be detected and evaluated.

Figure 1A:
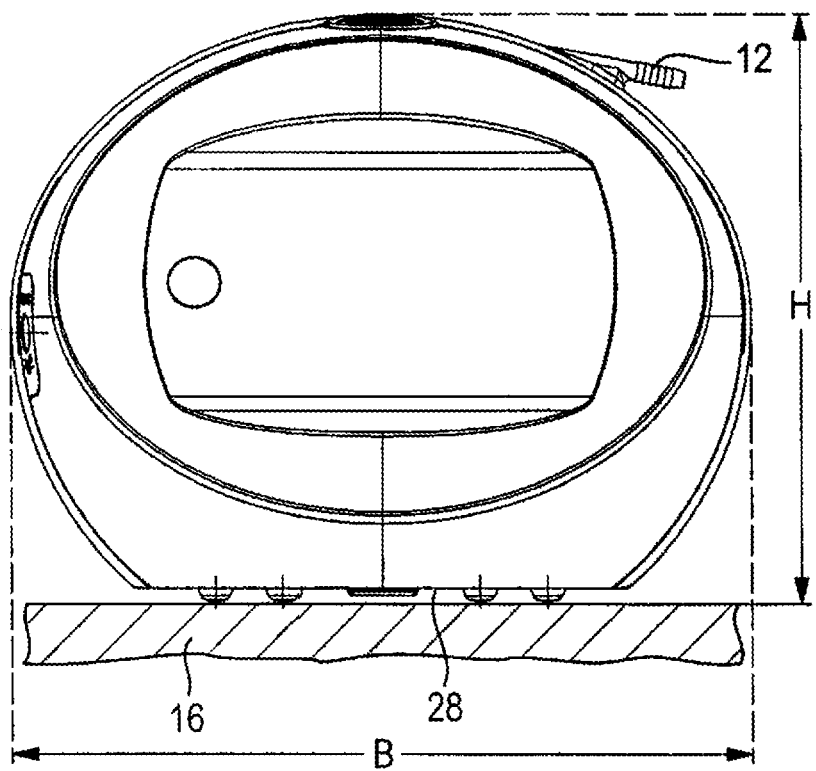
FIGS. 1a to e different views of a preferred embodiment of a device for carrying on the body to generate a vacuum for medical applications.
Figure 1B:
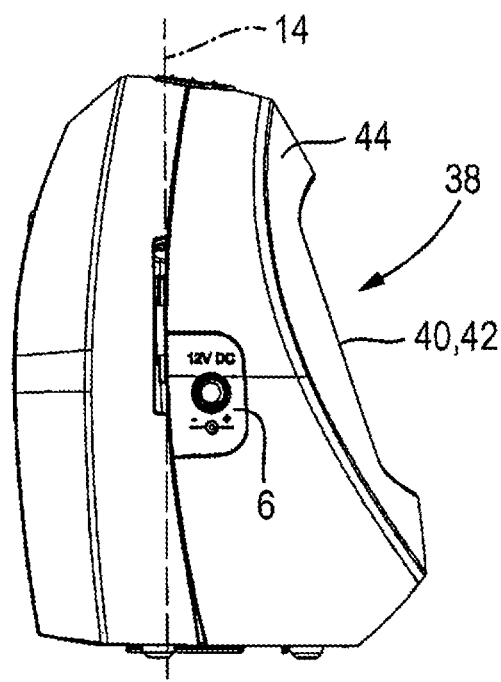
Figure 1C:
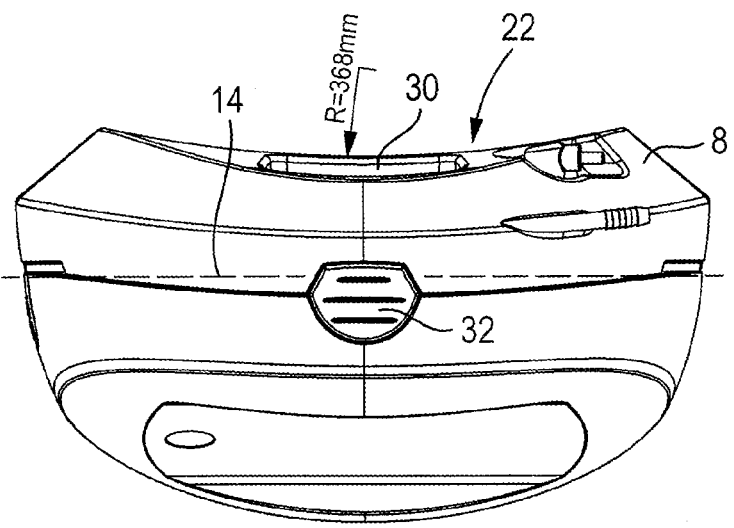
Figure 1D:
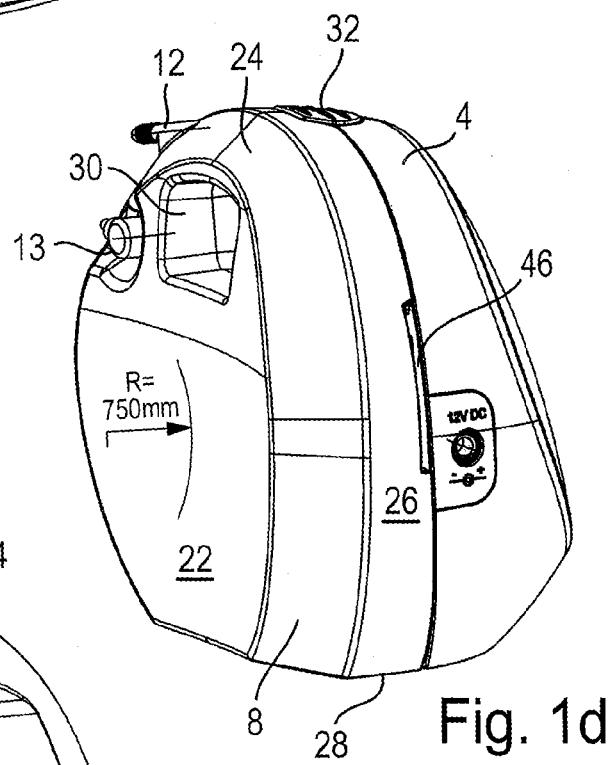
Figure 1E:
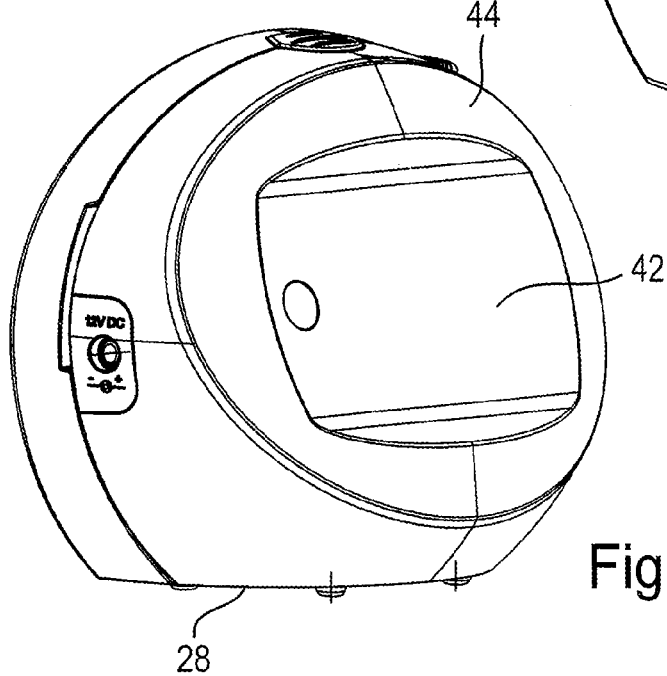

In the preferred case shown, the housing parts 4 and 8 lie one against the other on an essentially vertical separation plane 14 that is indicated in the various figures. When the device 2 is set down on an even horizontal surface 16, as shown in FIG. 1a, the separation plane 14 is oriented essentially vertically. This means that the two housing parts 4, 8 are not inserted one into the other nor stacked one upon the other, but that they remain side by side when the device 2 is joined as intended. The term separation plane 14 is therefore not to be understood as a geometrically level surface, as can be seen directly from FIGS. 2a to e, which show the first housing part 4 in various views. It is immediately apparent that the side 18 of the first housing part 4 facing the second housing part 8 is not level but formed with a multiplicity of elements projecting toward the second housing part 8. The side 20 of the second housing part 8 facing the first housing part 4 is constituted essentially complementarily to the shape of the side 18 of the first housing part 4 so that the two housing parts 4, 8 can only be joined and fastened together in the correct manner. The two housing parts 4, 8 are constituted disk-shaped overall, that is, their width B in the horizontal direction and their height H in the vertical direction are larger than their depth T in the horizontal direction and perpendicular to the extent of the width. In this way, it is possible for the device 2 to be constituted and dimensioned overall such that it can be comfortably worn on the body of the user. According to the invention, the device 2 is constituted such that the vessel parts 4, 8 disposed side by side can be positioned on the body in such a way that the second vessel part 8 is facing the body, that is, between the body and the first housing part 4 and the first housing part 4 is facing away from the body, that is, it essentially forms the visible side of the device 2. For that reason, the side 22 of the second housing part 8 facing the body of the user is beveled. As can be seen from FIGS. 1c, 1d, 3f, 3e, the side 22 facing the body is formed concavely seen in cross-section with a horizontal plane and comprises, for example, in the case shown, a radius of curvature R in some sections of, for example, 368 mm (FIGS. 1c, 3f). Additionally, the side 22 facing the body is also constituted concavely seen in cross-section with a vertical plane and has a radius of curvature R of, for example, 750 mm (FIG. 1d). In this way, the device 2 can be ergonomically disposed and worn in the hip region of a user.

It can also be seen that the second housing part 8 on its side 22 facing the body in an upper region and also on the side comprises a bevel 24 away from the body of the user toward the first housing part 4 or toward the side walls 26 and a circumferential facing end of the disk shape of the second housing part 8. The bevel 24, in the example shown here, runs round the full circumference; it extends from the standing side 28 from bottom to top, runs in an arc from there to the other side and then back down to the standing side 28.

It can also be seen from FIGS. 1d and 3 that, on the side 22 of the second housing part 8 facing the body, a grip recess 30 is formed in the shape of an opening extending right through the second housing part 8, and this in an upper region of the second housing part 8 slightly inclined away from the body. In this way, the device 2, or only its second housing part 8, can be gripped and handled with one hand.

Figure 2A:
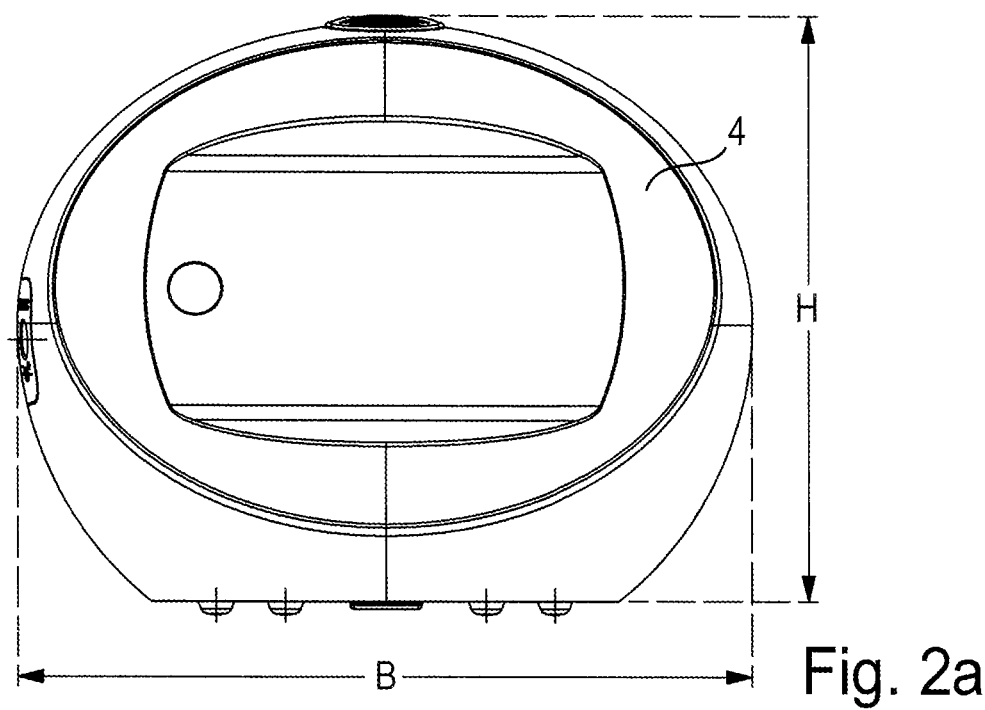
FIGS. 2a to e various views of a first housing part of the device according to FIG. 1, comprising a vacuum-producing facility and control components.
Figure 2B:
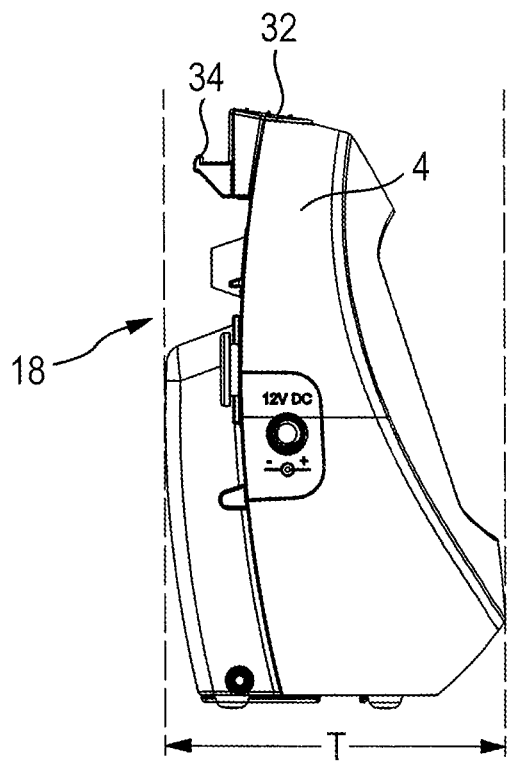
Figure 2C:
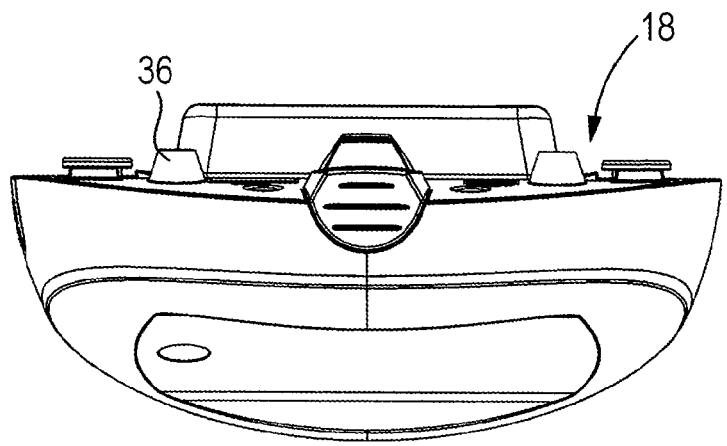
Figure 2D:
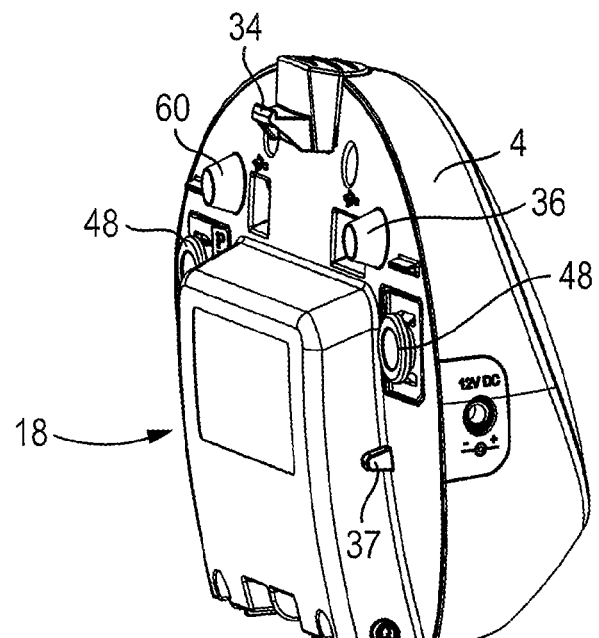
Figure 2E:
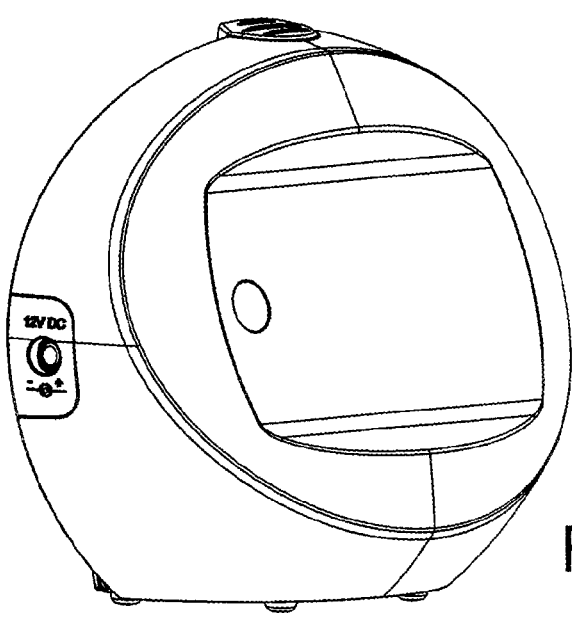
Figure 3D:
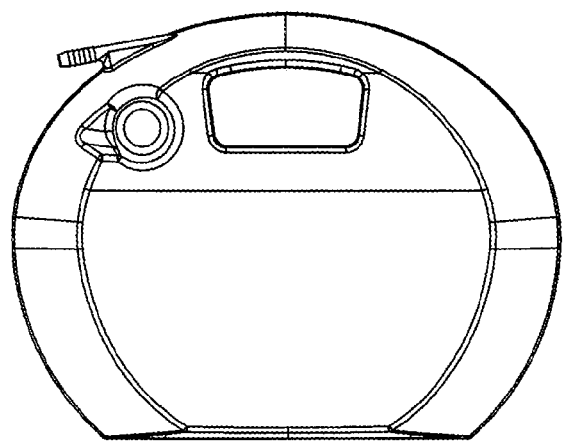
Figure 3G:
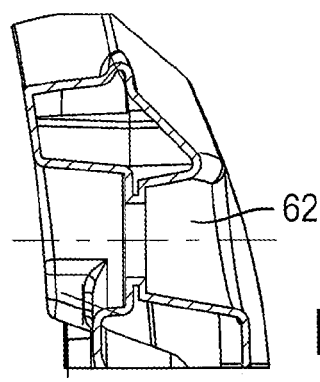
Figure 3H:
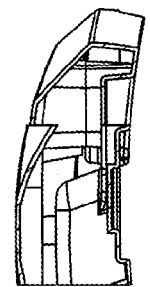
Figure 3I:
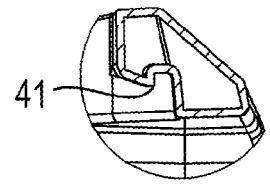
Figure 4A:
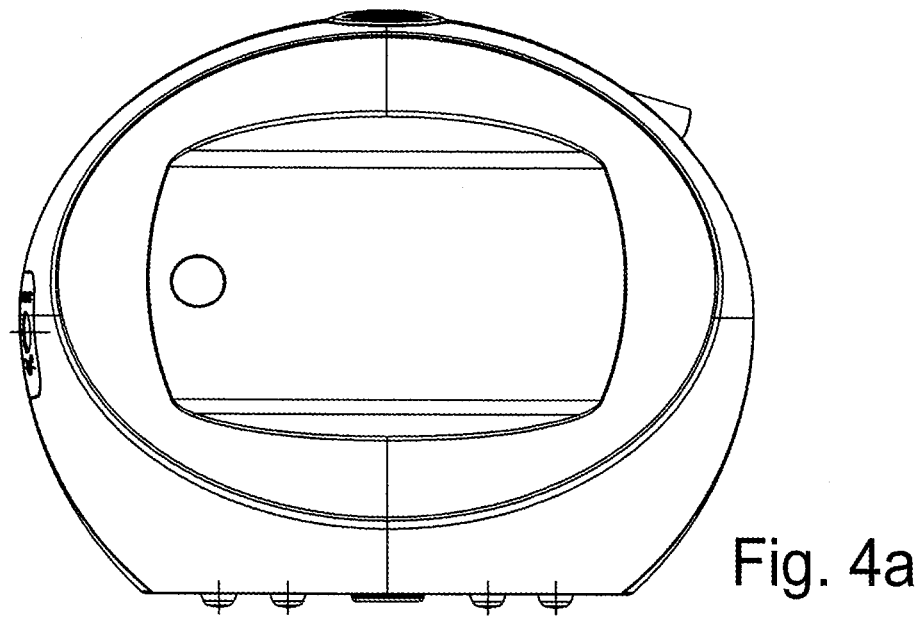
FIGS. 4a to e views corresponding to FIGS. 1a to e of a further embodiment of the device, wherein the second housing part is dimensioned larger than in the device according to FIGS. 1a to e.
Figure 4B:
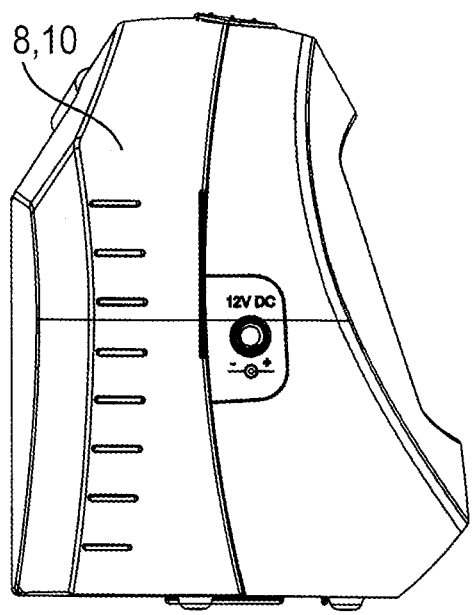
Figure 4C:
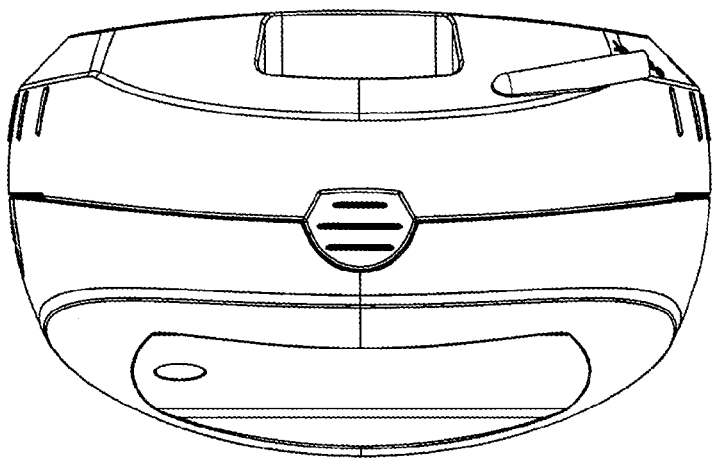
Figure 4D:
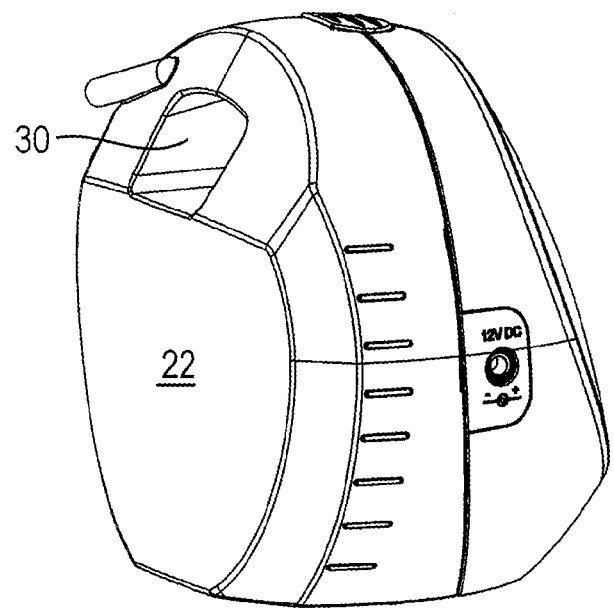
Figure 4E:
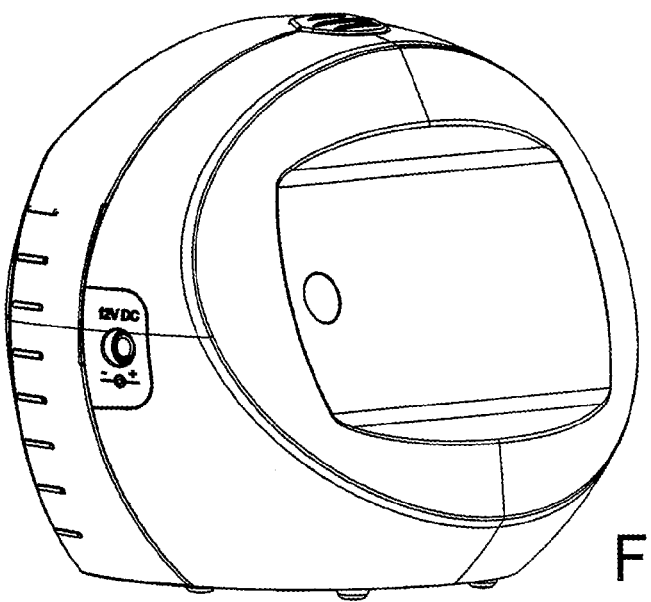

In the preferred embodiment shown, a manually operable element 32 is provided in this grip recess 30 on the upper side of the device 2, for example, in the form of a pushbutton that acts on the locking and back-gripping means 34 (see FIGS. 2b and 2d). In the joined condition of the two housing parts 4 and 8, the locking or back-gripping means 34 are in a locked condition holding the two housing parts 4,8 together by positive action. Only on operation of the operating element 32, is the lock released so that the housing parts 4, 8 can be separated. By the disposition and constitution of the grip recess 30 and the manually operable element 32 close together and such that a user can grip both in the grip recess 30 and also operate the operating element 32 with one finger of the same hand, a single-hand action for release of the second housing part 8 from the first housing part 4 is implemented. This proves especially advantageous because in that case a second housing part 8 filled with body fluids can be released with just one hand and placed in a disposal container.

To join the two housing parts 4, 8, the second housing part 8 is placed at a slight inclination from the rear and upward with its lower edge on two spigots forming a pivot 33 (FIG. 2d) of the first housing part 4. In the second housing part, a recessed region 35 (FIG. 3a) is formed on the lower edge to receive the spigot 33. If spigot 33 and the recessed region 35 are engaged, the second housing part 8 can be pivoted against the first housing part 4. In this way, the sides 18, 20 facing each other are placed one upon the other and thus enter the intended position with self-centering (supported by further guidance or centering means 37 (FIGS. 2d) and 39 (FIG. 3a) and the complementary shapes of the sides 18, 20 of the housing parts 4,8 facing each other). By moving the two housing parts 4, 8 one against the other, in particular, essentially transversely with respect to the vertical separation plane 14, the locking and back-gripping means 34 is automatically deflected and then latches in the position that locks the housing parts 4, 8 one against the other. For this purpose, on the second housing part 8 a latching hook 41 (FIG. 3i) is provided under which the locking or back-gripping means 34 grips. If the housing parts 4, 8 are put in their locked position, vacuum communication is then automatically established between the interior of the vessel 10 of the second housing part 8 and the vacuum-producing facility through connection means 36 (described later in connection with FIG. 5).

A visible side 38 of the first housing part 4 facing away from the body is constituted with a slight inclination from the vertical so that the shape of the disk tapers in the upward direction. In this way, the visible side 38 can be more easily seen. Operating elements 40 and display elements 42, in particular, in the form of a touchscreen are provided there. Essentially, the entire visible side 38 is overlapped or constituted by a large-surface cover 44 so that no dirt-trapping joints are formed in the region of the operating elements 40.

Moreover, the figures show, in the region of the separation plane 14 between the contacting housing parts 4, 8, a plug slot 46 for plugging and releasably fixing a fastening means, in particular, and preferably in the form of a flexible belt, or a bow or a strap, on which, for example, a belt or a carrying shoulder strap can be fastened, or in another form. It proves advantageous if this fastening means can be separated from the housing parts 4, 8 and is therefore no obstacle if the device 2 is used in stationary operation, that is, standing on a preferably level surface 16, for example, if a patient to be treated with the device 2 is resting in a hospital bed. FIG. 2d indicates, on the side 18 of the first housing part 4, means 48 on which the fastening means plugged into the plug slot 46 are fixed or held.

The further embodiment of the inventive device shown in FIGS. 4a to e differs from the embodiment shown in FIG. 3 in that the second housing part 8 and the vessel 10 constituted by it has a larger volume. The bevel in the upper region of the side 22 of the second housing part 8 facing the body, in which the grip cavity 30 is formed, is somewhat more inclined away from the body of the user. This permits even better access. This larger second housing part 8 is more suitable for stationary operation of the device 2; it could have an outwardly convex side 22 for this purpose or even be formed with a greater protrusion than is shown in FIG. 4.

Figure 5:
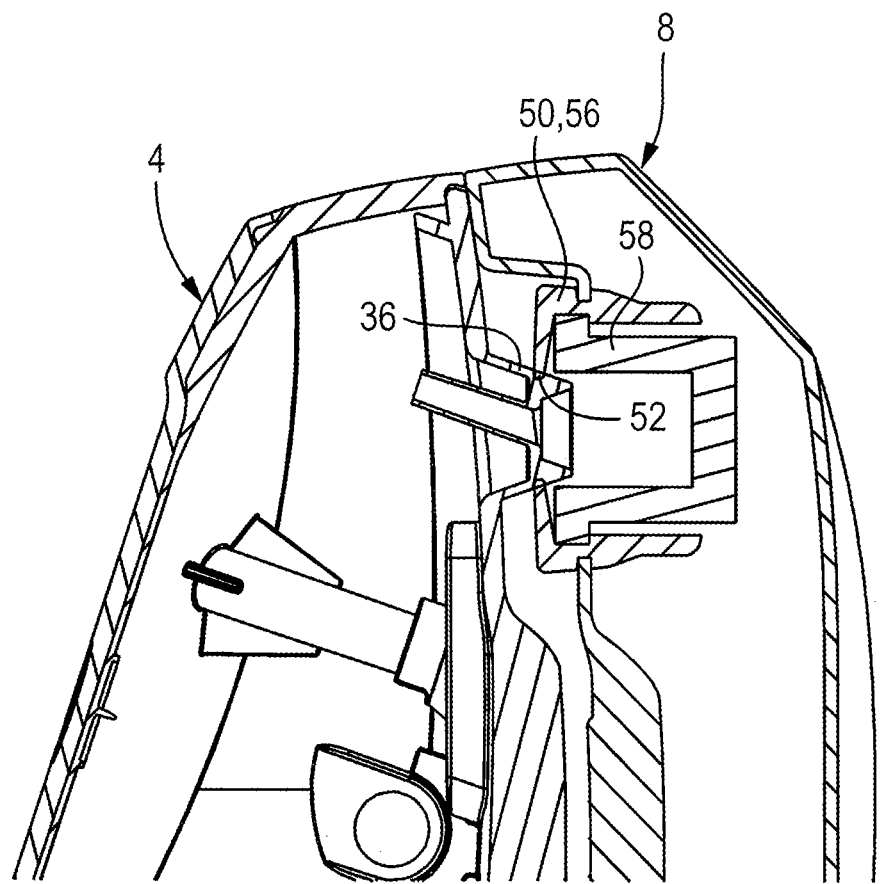
FIG. 5 a sectional view through the device in the region of the vacuum communication between the first and the second housing part.

FIG. 5 shows in detail the nature of the vacuum communication between the interior of the second housing part 8 constituting the vessel 10 and the first housing part 4. The suction side of a vacuum-producing facility, not depicted, leads to the conically shaped connection means 36 that tapers conically toward the second housing part 8. In this way, an at least slightly compliant mating connection means 50 of the second housing part 8 that, in the example shown, has a circular opening 52 that is bounded by a compliant sealing lip 54, can be applied with sealing, against the conical connection means 36 of the first housing part 4. This mating connection means 50 exits into the interior of the second housing part 8. It also forms a filter receiving means 56 for a filter 58 that, in the example shown, is constituted as a cup-shaped filter and prevents bacteria from being suctioned into the first housing part 4. It is immediately apparent that, on moving the two housing parts 4, 8 one against the other, the connection means 36 of the first housing part 4 forms a pressure communication sealed outwardly with the mating connection means 50 of the second housing part 8.

The coupling between the connection 13 for a measuring or rinsing duct and the associated also exemplary conically formed connection means 60 on the first housing part 4 is formed in a similar way. As can be seen from FIG. 3g, a coupling or grommet part, not depicted, can be inserted into the passage opening 62 in the second housing part 8 that then forms the connection 13 shown in FIG. 1d for the measuring or rinsing duct. This coupling or grommet part, not depicted, can then be coupled pressure-tight with the conical connection means 60. In this way, a fluid medium, in particular, air or a rinsing liquid can be guided into the wound through a tube to support the removal by suction of wound exudates. A measuring or rinsing tube and the suction tube are typically accessories for the second housing part that are single-use components; they are disposed of together with the second housing part after use.

FIG. 6 shows the previously described or similar device 2 for providing a vacuum for medical applications in a purely schematic representation, wherein relevant reference symbols are used for the corresponding components. However, FIG. 6 shows only the components that are relevant for the following description. FIG. 6 depicts a schematically indicated wound to be treated with a vacuum with a vacuum-tight wound dressing 80, to which the suction tube 82 emanating from the vessel 10 leads. From the vessel 10, a further tube section 84 leads outwardly through the already mentioned filter 58. If the vessel 10 or the first housing part 8 is put into its operating position on the first or basic housing part 4 of the device 2, the tube section 84 is connected to a further tube section 88 within the first housing part that leads to the intake side of the suction pump 90. This was described above only by way of example in FIG. 5. When the suction pump 90 operates, a vacuum is applied to the vessel 10 and to the suction tube 82 via tube sections 88, 84, and air suctioned in from there is blown out to the environment via outlet tube 92, wherein additionally non-depicted sound damping elements and, if necessary, further filters can be provided.

Moreover, a pressure sensor 94 for measuring the pressure is provided in the tube section 88 between vessel 10 and suction pump 90. Its signals are sent to an electronic control unit, collectively identified by reference symbol 100, which performs open-loop and closed-loop control of the device 2 in total. Also shown is the charging connection 6 for aforementioned rechargeable batteries that are located in a compartment 102 and a connection 104 for a schematically indicated power supply unit 106. With reference symbol 108, a display unit with a preferably provided capacitive switch membrane is indicated, via which operation of the device can be performed in total. The electrical connection to the electronic control unit 100 is only indicated via electrical lines 110. The suction pump 90 is controlled by the electronic control unit 100 in which, by means of the signals of the pressure sensor 94, a pressure and vacuum closed-loop control is implemented with known open-loop and closed-loop control mechanisms (setpoint/actual value control mechanisms), so that the pressure value corresponding to the currently selected program is controlled in the tube section 88.

Also shown is an additional rinsing or aeration tube 112 that, only in the case shown by way of example, leads through the vessel 10 and just like the suction tube 82 leads to the wound dressing 80. When the vessel 10 is attached in its intended assembly position on the first housing part 4, this rinsing tube 112 communicates with a tube section 114 provided in the first housing part 4 in which an electromagnetically operated valve 116 is provided that can be actuated by the electronic control unit 100 and connects the tube section 114 with the atmospheric air when it is open, so that an air current toward the wound via the rinsing tube 112 can be generated.

The device 2 and its electronic control unit 100 also feature a data interface 118, preferably a USB interface, by means of which the electronic control unit 100 or its method of operation can be programmed.

According to the invention, the electronic control unit 100 is constituted in such a way that the vacuum-producing suction pump 90 is permanently deactivated if a rate of pressure change ($\Delta p/\Delta t$) determined by means of the signals of the pressure sensor 94 exceeds a defined threshold value toward decreasing vacuum, that is, toward increasing absolute pressure. In the overwhelming majority of cases, this is due to intentional or unintentional detachment of the vessel 10 from the first or basic housing part 4. This state of deactivation of the closed-loop pressure control operation or the suction pump 90 is then visually output via the display unit, if necessary, an acoustic signal is, additionally or alternatively, output via a loudspeaker 120. This avoids an undifferentiated state during closed-loop vacuum control operation, in particular, controlling the suction pump toward greater suction. In this way, defined states are used and the user is familiarized with the fact that he must perform a restart of the system on intentional or unintentional detachment of the vessel.

It further proves especially advantageous that the electronic control unit 100 does not deactivate the suction pump on a vacuum increase in the tube section 88 between vessel 10 and suction pump 90 that points to increasing filling of the vessel, but continues the defined closed-loop vacuum control operation. For example, if this vacuum increase, that is, a reduction in absolute pressure, has only occurred because the liquid-tight filter 58 is blocked briefly due to inclination of the vessel 10 resulting from the mobility of the user, without the vessel 10 already being so full that a vessel change is appropriate, or another only temporary blockage or disconnection of a tubing means has occurred. But, irrespective of this, it also proves advantageous that deactivation of the closed-loop pressure control operation and the suction pump 90 due to disturbance only occurs if an abrupt increase in pressure, that is, abrupt decrease in vacuum is detected in the tube section 88 between the vessel 10 and suction pump 90, which is ascertained by determining and comparing the rate of pressure change $\Delta p/\Delta t$ toward decreasing vacuum with a defined threshold value.

We claim:

1. A method for operating a portable device to generate a vacuum for medical vacuum treatment of wounds on a body of humans or animals, the device comprising:
 a first housing part, said first housing part accommodating a vacuum-producing suction pump;
 a vessel for receiving body liquids or wound exudates suctioned out of a wound, said vessel structured for releasable attachment to said first housing part, wherein vacuum is applied by said suction pump in an attached condition of said vessel, said vessel having a connection for a suction tube leading to the body for the establishment of vacuum communication between said suction pump, said vessel and the suction tube;
 a pressure sensor disposed between said vessel and said suction pump to measure a pressure in a tube section; and
 a programmable electronic control unit connected to said suction pump and to said pressure sensor for controlling operation of said suction pump in dependence on defined parameters and on pressure values measured by said pressure sensor, said electronic control unit being disposed, structured and dimensioned to deactivate said suction pump if, during continuing closed-loop vacuum control operation, a rate of change in pressure ($\Delta p/\Delta t$) detected body said pressure sensor exceeds a defined threshold value toward decreasing vacuum,
the method comprising the steps of:
 using, by means of said electronic control unit, signals of said pressure sensor to determine a rate of pressure change ($\Delta p/\Delta t$) and, upon decreasing vacuum and increasing absolute pressure, the rate of pressure change ($\Delta p/\Delta t$) is compared with a threshold value stored in said control unit, and said suction pump is deactivated when said threshold value is exceeded.

2. The method of claim 1, wherein said threshold value is 40 mmHg/s or higher.

3. The method of claim 1, wherein the device further comprises an output or display unit for generating a signal that visually or acoustically communicates an abrupt increase in pressure with a rate of pressure change above said threshold value.

4. The method of claim 1, wherein the device further comprises an output or display unit constituted for wireless communication of a signal to an external receiver that communicates an abrupt pressure increase with a rate of pressure change above said threshold value to said external receiver.

5. The method of claim 1, wherein the device further comprises an aeration valve which is controlled by said electronic control unit and connected to a wound space via an addition aeration tube to aerate the wound space with fresh air.

6. The of claim 1, wherein the device further comprises a facility controlled by said electronic control unit to supply a rinsing liquid or other fluid to a wound space via an additional rinsing tube.

7. The method of claim 6, wherein said electronic control unit is constituted such that it also deactivates said facility for supplying a rinsing liquid or other fluid upon deactivation of said suction pump.

8. The method of claim 1, wherein said electronic control unit is constituted in such a way that, upon correct or incorrect detection of a vessel-full state, said suction pump is not deactivated but continues a defined, closed-loop vacuum control operation.

9. The method of claim 1, wherein said electronic control unit is constituted in such a way that, upon vacuum increase and decrease in an absolute pressure in a tube section disposed between said vessel and said suction pump, said suction pump is not deactivated, rather continues a defined closed-loop vacuum control operation.

10. The method of claim 9, wherein said vacuum increase points to increasing filling of said vessel.

11. The method of claim 1, wherein, upon vacuum increase and decrease in an absolute pressure value in a tube section disposed between said vessel and said suction pump, said suction pump is not deactivated, but a defined closed-loop vacuum control operation is continued.

12. The method of claim 11, wherein said vacuum increase points to increasing filling of said vessel.

* * * * *